United States Patent [19]

Szántay et al.

[11] 4,054,571
[45] Oct. 18, 1977

[54] NITROGEN-CONTAINING POLYCYCLIC COMPOUNDS AND A PROCESS FOR THE PREPARATION THEREOF

[75] Inventors: Csaba Szántay; Lajor Szabó; Gyorgy Kalaus; Egon Kárpáti; László Szporny, all of Budapest, Hungary

[73] Assignee: Richter Gedeon Vegyeszeti Gyar Rt., Budapest, Hungary

[21] Appl. No.: 614,151

[22] Filed: Sept. 17, 1975

[30] Foreign Application Priority Data

Sept. 27, 1974 Hungary ............................... RI-546

[51] Int. Cl.$^2$ ............................................. C07D 471/04
[52] U.S. Cl. .............................. 260/293.55; 260/296 P
[58] Field of Search ........................................ 260/293.55

[56] References Cited
PUBLICATIONS

Wieland, et al., C.A. vol. 51: 7370-7372 (1957).

Primary Examiner—Cecilia M. S. Jaisle
Attorney, Agent, or Firm—Toren, McGeady and Stanger

[57] ABSTRACT

The invention relates to new eburnamenine derivatives of the general formula (I),

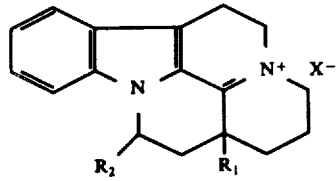

wherein
$R_1$ stands for an alkyl group,
$R_2$ stands for a carboxy group, a functional carboxy derivative (preferably an ester group) or a group convertable into carboxy group or a functional derivative thereof (preferably cyano group), and $X^-$ is an anion derived from an acid, and the corresponding free bases.

These compounds are valuable intermediates of the preparation of eburnamenine derivatives with advantageous therapeutical effects.

The above compounds are prepared as follows: a compound of the general formula (II),

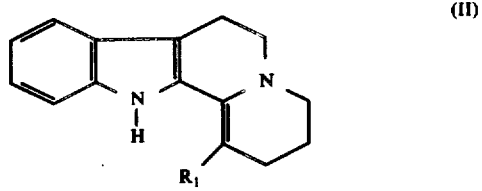

wherein $R_1$ has the same meanings as defined above, is reacted with a compound of the general formula (III),

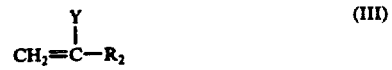

wherein $R_2$ has the same meanings as defined above and Y is halogen, and, if desired, a thus-obtained compound of the general formula (I), wherein $R_1$ and $R_2$ each have the same meanings as defined above and $X^-$ is a halide ion, is reacted with an acid, and/or, if desired, a compound of the general formula (I), wherein $R_1$ and $X^-$ each have the same meanings as defined above and $R_2$ is cyano or an ester group, is subjected to hydrolysis, and/or, if desired, a compound of the general formula (I), wherein $R_1$, $R_2$ and $X^-$ each have the same meanings as defined above, is treated with a base.

7 Claims, No Drawings

NITROGEN-CONTAINING POLYCYCLIC COMPOUNDS AND A PROCESS FOR THE PREPARATION THEREOF

This invention relates to new indolopyrido-naphthyridine derivatives and their salts, as well as to a process for the preparation thereof.

The new compounds according to the invention can also be regarded as the derivatives of the alkaloid eburnamenine (J. Org. Chem. 28, 2197/1963/). For this reason the new compounds according to the invention are termed in the following as the derivatives of eburanamenine.

According, the invention relates to new eburnamenine derivatives having the general formula (I),

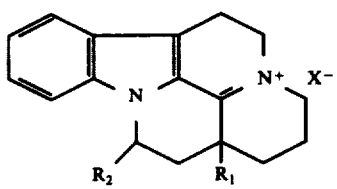

wherein
$R_1$ stands for an alkyl group,
$R_2$ stands for a carboxy groyp, a functional carboxy derivative (preferably an ester group) or a group convertable into carboxy group or a functional derivative thereof (preferably cynao group), and
$X^-$ is an anion derived from an acid,
as well as to the corresponding free bases.

The new compounds according to the invention can be used as intermediates or starting substances in the synthesis of eburnamenine derivatives with valuable therapeutical effects.

In the compounds of the general formula (I) $R_1$ represents a straight-chained or branched alkyl group, preferably a lower alkyl group with 1 to 6 carbon atoms. Of these groups e.g. the methyl, ethyl, n-propyl, isopropyl, n-butyl, isobutyl, tert-butyl, amyl, isoamyl and hexyl groups are to be mentioned. Particularly preferred are those compounds of the general formula (I), in which $R_1$ stands for ethyl.

$R_2$, when it stands for an ester group, may represent e.g. an alkoxy carbonyl or aralkyloxycarbonyl group. The alkoxycarbonyl groups contain preferably a straight-chained or branched $C_{1-6}$ alkoxy group; of these e.g. the methoxycarbonyl, ethoxycarbonyl, n-propoxycarbonyl, n-butyoxycarbonyl, isobutoxycarbonyl, tert-butoxycarbonyl, amloxycarbonyl, isoamyloxycarbonyl, n-hexyloxycarbonyl and isohexyloxycarbonyl groups are to be mentioned. The preferred aralkoxycarbonyl groups are mono- or polycyclic, and contain a $C_7-_{20}$ aralkoxy groups; of those e.g. the benzyloxycarbonyl, phenethoxycarbonyl, phenylpropoxycarbonyl, phenylbutoxycarbonyl, naphthylmethoxycarbonyl, naphthylethoxycarbonyl and naphthylbutoxycarbonyl groups are to be mentioned.

In the compounds of the general formula (I) $X^-$ may stand for an anion derived from any organic or inorganic acid. Of these anions e.g. the following are to be mentioned: halides, such as fluoride, chloride, bromide and iodide, sulfate, phosphate, a perhalogenate, such as perchlorate and perbromate, acetate, propionate, oxalate, citrate, benzoate, naphthoate, maleate, succinate, salicylate, p-toluenesulfonate, etc.

The most preferred compounds of the general formula (I)are the ones in which $R_1$ stands for a lower alkyl group, $R_2$ represents a carboxy, lower alkoxycarbonyl or cyano group, and $X^-$ is an anion derived from an acid.

Particularly preferred are those compounds of the general formula (I), in which $R_1$ stands for ethyl or n-butyl, $R_2$ stands for methoxycarbonyl, ethoxycarbonyl or cyano, and $X^-$ is perchlorate.

The compounds of the general formula (I) and the corresponding free bases can be prepared in accordance with the invention by reacting a compounds of the general formula (II),

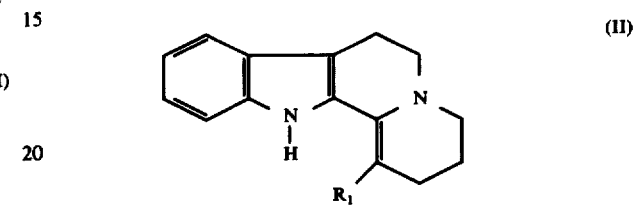

wherein $R_1$ has the same meanings as defined above, with a compound of the general formula (III),

wherein $R_2$ has the same meanings as defined above and Y is halogen, and, if desired, reacting a thus-obtained compound of the general formula (I), wherein $R_1$ and $R_2$ each have the same meanings as defined above and $X^-$ is a halide ion, which an acid, and/or, if desired, subjecting a compound of the general formula (I), wherein $R_1$ and $X^-$ each have the same meanings as defined above and $R_2$ is cyano or an ester group, to hydrolysis, and/or, if desired, treating a compound of the general formula (I), wherein $R_1$, $R_2$ and $X^-$ each have the same meanings as defined above, with a base.

The starting substances of the general formula (II) can be prepared by the method of E. Wenkert et al. (J. Am. Chem. Soc. 87, 1580/1965/) by treating 1-(3-indolyl-ethyl)-3-ethyl-piperidinone-2 with phosphorous oxychloride. The starting substance of this reaction can be prepared as follows: diethyl malonate is converted into ethyl-γ-bromo-propylmalonic acid diethyl ester, this substance is hydrolyzed and decarboxylated by boiling it with hydrogen bromide, the obtained substance is esterified with diazomethane, and the resulting methyl 2-ethyl-5-bromo-valerate is condensed with tryptamine. Alternately, the compounds of the general formula (II) can also be prepared by reacting an α-alkyl-δ-hydroxypentanoyl-tryptamide with phosphorous oxychloride.

The α-halogenated acrylic acid derivatives of the general formula (III) can be prepared as described in J. Am. Chem. Soc. 61, 3156 (1939).

The meanings of $R_1$ and $R_2$ in the compounds of the general formulae (II) and (III) are preferably the same as listed in connection with the compounds having the general formula (I). In the compounds of the general formula (III) Y may stand for any halogen atom, such as fluorine, bromine, chlorine or iodine, but Y represents preferably a chlorine or bromine atom.

The compounds of the general formula (II) are applied in accordance with the invention, preferably in the form of their salts, of which the acid addition salts, such as the perhalogenates (e.g. the perchlorates, perbromates, etc.) are particularly suitable. If the starting substances of the general formula (II) are used in the form of their acid addition salts, these compounds are treated with a base before reacting them with a compound of the general formula (III), preferably directly in the reaction mixture, and the resulting free bases of the general formula (II) are reacted with the compounds of the general formula (III). In this reaction preferably a dilute aqueous solution of an inorganic base, e.g. an alkali metal hydroxide, such as sodium hydroxide, potassium hydroxide, etc., is used. The base is generally used in an excess of 20 to 40% related to the stoichiometric amount. The bases of the general formula (II) are liberated from their salts preferably in an inert, organic, water-immiscible solvent, such as a halogenated hydrocarbon (e.g. chloroform, carbon tetrachloride, dichloromethane, 1,2-dichloroethane, trichloroethylene, etc.). The reaction is performed preferably under an inert gas, such as nitrogen or argon. As the reaction is performed in heterogeneous phase, it is preferable to ensure steady stirring. The reaction temperature may vary within wide limits, the reaction is performed, however, preferably at room temperature. Thereafter the organic phase is separated, dried, and the reactant of the general formula (III) is added. The compounds of the general formula (III) are applied preferably in excess, such as in an amount of 2 to 8 moles, particularly 4 to 5 moles for one mole of the starting substance of the general formula (II). The reaction time and temperature are not critical, it is preferable, however, to allow the mixture to stand at room temperature for 1 to 4 days.

The reaction mixture can be processed by known methods. Thus, for instance, if a solution is obtained, the solvent is evaporated, preferably under reduced pressure.

The reaction of the compounds having the general formulae (II) and (III) yields compounds of the general formula (I) wherein $R_2$ and $R_1$ each have the same meanings as defined above and $X^-$ is a halide ion. These compounds can be reacted with another acid, if desired. This reaction is performed preferably by dissolving the respective halide in a cold or warm inert solvent, preferably in an aliphatic alcohol, such as methanol, ethanol, etc., and adding the appropriate acid to this solution.

The acid addition salts of the general formula (I), wherein $R_1$, $R_2$ and $X^-$ each have the same meanings as defined above, can be converted, if desired, into the corresponding free bases by reacting them with a base. In this reaction preferably an aqueous solution of an inorganic base, such as an alkali metal hydroxide, e.g. sodium hydroxide, is used. This reaction can be carried out preferably by suspending a salt of the general formula (I) in water, adding to the suspension an inert organic solvent, e.g. a halogenated hydrocarbon, such as dichloromethane, and introducing the base into the suspension under stirring and cooling. These operations are performed preferably under inert atmosphere.

The compounds of the general formula (I), wherein $R_1$ and $X^-$ have the same meanings as defined above and $R_2$ stands for cyano or an ester group, as well as the corresponding free bases can be subjected optionally to hydrolysis, to obtain compounds of the general formula (I), wherein $R_2$ stands for carboxy, or the corresponding free bases.

The hydrolysis is performed preferably in an inert organic solvent, particularly in an aliphatic alcohol, such as ethanol, with a base, preferably an inorganic base, such as an alkali metal hydroxide (e.g. sodium hydroxide) as hydrolyzing agent.

The reaction mixtures can be processed by methods known per se. The actual method of processing depends on the nature of the starting substances, the end-products, the solvents, etc. If the product separates at the end of the reaction, it is isolated by filtration, whereas if it remains dissolved, the solution is evaporated to dryness, preferably under reduced pressure.

The end-products and intermediates formed in the process of the invention can generally be separated from the reaction mixture in crystalline state. If, however, an oily substace is obtained, this can be converted easily into amorphous powder by triturating it with an apolar solvent, such as an ether, petroleum ether, etc.

If desired, the compounds of the general formula (I) can be subjected to additional purification steps, such as recrystallization. As solvents for recrystallization e.g. aliphatic alcohols, such as methanol or ethanol, ketones, such as acetone, aliphatic esters, particularly alkyl alkanecarboxylates, such as ethyl acetate, acetonitrile, etc. can be used.

The process of the invention enables to produce the compounds of the general formula (I) with high yields and in forms easy to identify. The analytical data of the obtained compounds are in good agreement with the calculated values. The structures of the obtained products can be confirmed further by IR and NMR spectroscopy.

The invention is elucidated in detail by the aid of the following non-limiting Examples.

EXAMPLE 1

3,4-Dehydro-14,15-dihydro-14-methoxycarbonyleburnamenine perchlorate 4.0 g (11.4 mmoles) of 1-ethyl-1,2,3,4,6,7-hexahydro-12H-indolo(2,3-a)quinolizinium perchlorate (J. Am. Chem. Soc. 87, 1580/1968/) are suspended in 40 ml. of dichloromethane, and 30 ml. of distilled water and 8 ml. of a 2 n aqueous sodium hydroxide solution are added to the stirred suspension under argon atomsphere. The reaction mixture is stirred for 10 minutes, thereafter the organic phase is separated and dried over anhydrous potassium carbonate. The drying agent is filtered off, 4 ml. of freshly distilled methyl α-bromo-acrylate are added to the filtrate, the mixture is flushed with argon, and it is allowed to stand at room temperature. Exothermic reaction sets in and the colour of the solution turns lighter. After two days of standing at room temperature the solution is evaporated in vacuo, and the oily residue is repeatedly triturated with petroleum ether. The obtained solid is dissolved in 10 ml. of methanol, and 2.0 ml. of 70% perchloric acid solution are added. The crystallization is initiated by scraping the wall of the flask, thereafter the mixture is maintained in refrigerator. The separated crystals are filtered off and washed with cold methanol to obtain 4.65 g. of a yellow substance.

This substance is recrystallized from 8-fold volume of methanol to obtain 4.20 g. (84.6%) of 3,4-dehydro-14,15-dihydro-14-methoxycarbonyl-eburnamenine perchlorate as a yellow, crystalline substance melting at 188°-190° C.

Analysis: calculated for $C_{21}H_{25}N_2O_6Cl$ (M = 436.88): C: 57.73 %; H: 5.76 %; N: 6.41 %; found: C: 57.93 %; H: 5.66 %; N: 6.50 %

IR-spectrum (in KBr pellet): 1748 cm$^{-1}$ (=C=O) and 1642 cm$^{-1}$ (=C=N$^+$=)—

EXAMPLE 2

3,4-Dehydro-14,15-dihydro-14-ethoxycarbonyleburnamenine perchlorate 4.0 g. (11.4 mmoles) of 1-ethyl-1,2,3,4,6,7-hexahydro12H-indolo(2,3-a)quinolizinium perchlorate are suspended in 40 ml. of dichloromethane, and 30 ml. of distilled water and 8 ml. of a 2 n aqueous sodium hydroxide solution are added to the stirred suspension under argon atmosphere. The reaction mixture is stirred for 10 minutes, thereafter the organic phase is separated and dried over anhydrous potassium carbonate. The drying agent is filtered off, 4 ml. of freshly distilled ethyl α-bromo-acrylate are added to the filtrate, the mixture is flushed with argon, and it is allowed to stand at room temperature. Exothermic reaction sets in and the colour of the solution turns lighter. After two days of standing at room temperature the solution is evaporated in vacuo, and the oily residue is repeatedly triturated with petroleum ether. The obtained solid is dissolved in 10 ml. of hot ethanol, and 2.0 ml. of a 70% perchloric acid solution are added to the hot solution, whereupon crystals separate. The mixture is maintained in a refrigerator. The separated yellow crystals are filtered off and washed with cold ethanol to obtain 4.35 of a crystalline substance.

This substance is recrystallized twice from ethanol to obtain 3.0 g. (58.6 %) of 3,4-dehydro-14,15-dihydro-14-ethoxycarbonyl-eburnamenine perchlorate as a yellow crystalline substance melting at 191°–193° C.

Analysis: calculated for $C_{22}H_{27}N_2ClO_6$ (M = 450.91): C: 58.59 %; H: 6.03 %; N: 6.21 %; found: C: 58.80 %; H: 5.72 %; N: 6.20 %

IR spectrum (in KBr pellet): 1736 cm$^{-1}$ (=C=O) and 1643 cm$^{-1}$ (=C=N$^+$=).

EXAMPLE 3

3,4-Dehydro-14,15-dihydro-14-cyano-eburnamenine perchlorate 2.0 g (5.67 mmoles) of 1-ethyl-1,2,3,4,6,7-hexahydro-12H-indolo(2,3-a)quinolizinium perchlorate are suspended in 20 ml. of dichloromethane, and 15 ml. of distilled water and 4 ml. of a 2 n aqueous sodium hydroxide solution are added to the stirred suspension under argon atomsphere. The reaction mixture is stirred for 10 minutes, thereafter the organic phase is separated and dried over anhydrous potassium carbonate. The drying agent is filtered off, 2.0 ml. (25.2 mmoles) of α-chloro-acrylonitrile are added to the filtrate, the mixture is flushed with argon, and it is allowed to stand at room temperature. Exothermic reaction sets in and the colour of the solution turns lighter. After 2-3 days of standing at room temperature the reaction mixture is evaporated in vacuo, the solid residue is dissolved in 6 ml. of hot methanol, and a 70% perchloric acid solution is added. A light yellow, crystalline substance starts immediately to separate. The mixture is kept in a refrigerator, the crystals are filtered off, and the obtained 2.25 g. of crude substance is recrystallized from threefold volume of methanol. 2.0 g. (87.8 %) of 3,4-dehydro-14,15-dihydro-14-cryano-eburnamenine perchlorate are obtained as a light yellow, crystalline substance melting at 240° to 241° C under decomposition.

Analysis: calculated for $C_{20}H_{22}N_3ClO_4$ (M = 403.85): C: 59.47 %; H: 5.49 %; N: 10.44 %; found: C: 59.54 %; H: 5.51 %; N: 10.23 %

IR-spectrum (in KBr pellet): 2320 cm$^{-1}$ (-CN) and 1631 cm$^{-1}$ (=C=N$^+$=).

EXAMPLE 4

3,4-Dehydro-14,15-dihydro-14-methoxycarbonyl-21-ethyl-eburnamenine perchlorate 5.0 g. (13.3 mmoles) of 1-n-butyl-1,2,3,4,6,7-hexahydro-12H-indolo(2,3-a)quinolizinium perchlorate are suspended in 50 ml. of dichloromethane, and 40 ml. of distilled water and 10 ml. of a 2 n aqueous sodium hydroxide solution are added to the stirred suspension under argon atmosphere. The reaction mixture is stirred for 10 minutes, thereafter the organic phase is separated and dried over anhydrous potassium carbonate. The drying agent is filtered off, 5.0 ml. of freshly distilled methyl α-bromo-acrylate are added to the filtrate, the mixture is flushed with argon, and it is allowed to stand at room temperature. After 3 days of standing at room temperature the reaction mixture is evaporated in vacuo, the obtained red, oily residue is dissolved in 10 ml. of hot methanol, the solution is filtered, and 2.30 ml. of a 70% perchloric acid solution are added dropwise to the filtrate. Upon cooling, a yellow, crystalline substance separates from the solution, This substance is filtered off, washed with a small amount of methanol, and the crude product, weighing 4.75 g., is recrystallized from 15-fold volume of methanol. 4.20 g. (68.0 %) of 3,4-dehydro-14,15-dihydro-14-methoxycarbonyl-21-ethyl-eburnamenine perchlorate are obtained. as a dense, crystalline substance melting at 147°–148° C.

Analysis: calculated for $C_{23}H_{29}N_2ClO_6$ (M = 464.93): C: 59.41 %; H: 6.28 %; N: 6.02 %; found: C: 59.30 %; H: 6.20 %; N: 6.20 %;

IR-spectrum (in KBr pellet): 1752 cm$^{-1}$ (=C=O) and 1648 cm$^{-1}$ (=C=N$^+$=).

EXAMPLE 5

2,3-Dehydro-14,15-dihydro-14-cyano-21-ethylburnamenine perchlorate 5.0 g. (13.3 mmoles) of 1-n-butyl-1,2,3,4,6,7-hexahydro-12H-indolo(2,3-a)quinolizinium perchlorate are suspended in 50 ml. of dichloromethane, and 40 ml. of distilled water and 10 ml. of a 2 n aqueous sodium hydroxide solution are added to the stirred suspension under argon atmosphere. The reaction mixture is stirred for some minutes, thereafter the organic phase is separated and dried over anhydrous potassium carbonate. The drying agent is filtered off, 5.0 ml. of α-chloro-acrylonitrile are added to the filtrate, the mixture is flushed with argon, and it is allowed to stand at room temperature. Exothermic reaction sets in, and the colour of the solution turns lighter. After 3 days of standing at room temperature the reaction mixture is evaporated in vacuo, the residue is dissolved in 15 ml. of hot methanol, and 2.20 ml. of a 70% perchloric acid solution are added. Upon cooling, a yellow, crystalline substance separates from the solution. The mixture is kept in a refrigerator, and subsequently the crystals are filtered off. 3.50 g. (61.0 %) of 3,4-dehydro-14,15-dihydro-14-cyano-21-ethyl-eburnamenine perchlorate are obtained; m.p.: 259°–260° C under decomposition.

Analysis: calculated for $C_{22}H_{26}N_3ClO_4$ (M = 431.90): C: 61.17 %; H: 6.15 %; N: 9.69 %; found: C: 61.34 %; H: 6.15 %; N: 9.69 %

IR-spectrum (in KBr pellet ): 2360 cm$^{-1}$(—CN), and 1648 cm$^{-1}$(=C=N$^+$=).

What we claim is:

1. A compound of the formula (I),

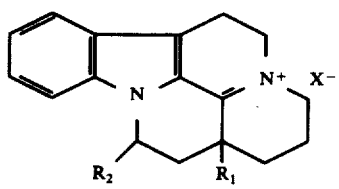

wherein $R_1$ is a lower alkyl group with 1 to 6 carbonyl group having 1 to 6 carbon atoms in the alkoxy moiety, an aralkoxycarbonyl group having 7 to 20 carbon atoms in the aralkoxy moiety or a cyano group, and $X^-$ is an anion derived from an acid, and the corresponding free base.

2. 3,4-Dehydro-14,15-dihydro-14-methoxycarbonyleburnamenine perchlorate.

3. 3.4-Dehydro-14,15-dihydro-14-ethoxycarbonyleburnamenine perchlorate.

4. 3,4-Dehydro-14,15-dihydro-14-cyano-eburnamenine perchlorate.

5. 3,4-Dehydro-14,15-dihydro-14-methoxycarbonyl-1-ethyleburnamenine perchlorate.

6. 3,4-Dehydro-14,15-dihydro-14-cyano-21-thyleburnamenine perchlorate.

7. A process for the preparation of an eburnamenine erivative of the formula (I)

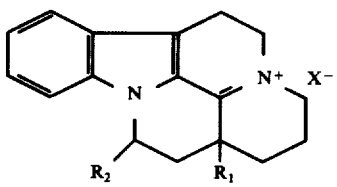

wherein $R_1$ is a lower alkyl group with 1 to 6 carbon atoms,
$R_2$ is a carboxy group, an alkoxycarbonyl group having 1 to 6 carbon atoms in the alkoxy moiety, an aralkoxycarbonyl group having 7 to 20 carbon atoms in the aralkoxy moiety or a cyano group, and
$X^-$ is an anion derived from an acid,
and of the corresponding free base, which comprises reacting a compound of the formula (II),

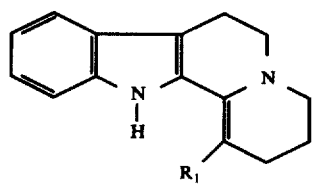

wherein
$R_1$ has the same meaning as above, with a compound of the formula (III),

wherein
$R_2$ has the same meanings as above and Y is halogen.

* * * * *